(12) United States Patent
Khait et al.

(10) Patent No.: US 8,911,360 B2
(45) Date of Patent: Dec. 16, 2014

(54) SYSTEM AND METHOD FOR CONTROLLING POWER CONSUMPTION OF AN IN VIVO DEVICE

(75) Inventors: Semion Khait, Tiberias (IL); Eli Horn, Kiryat Motzkin (IL); Micha Nisani, Ramot Itzhak (IL); Ofra Zinaty, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 43 days.

(21) Appl. No.: 13/510,712

(22) PCT Filed: Nov. 18, 2010

(86) PCT No.: PCT/IL2010/000972
§ 371 (c)(1),
(2), (4) Date: Jul. 10, 2012

(87) PCT Pub. No.: WO2011/061746
PCT Pub. Date: May 26, 2011

(65) Prior Publication Data
US 2012/0271104 A1 Oct. 25, 2012

Related U.S. Application Data

(60) Provisional application No. 61/263,121, filed on Nov. 20, 2009.

(51) Int. Cl.
*A61B 1/00* (2006.01)
*A61B 1/04* (2006.01)
*A61B 1/045* (2006.01)

(52) U.S. Cl.
CPC .............. *A61B 1/041* (2013.01); *A61B 1/00029* (2013.01); *A61B 1/00036* (2013.01); *A61B 1/00032* (2013.01); *A61B 2560/0209* (2013.01); *A61B 1/045* (2013.01)
USPC .......................................... 600/118; 600/117

(58) Field of Classification Search
USPC .................................................. 600/109, 160
See application file for complete search history.

(56) References Cited

U.S. PATENT DOCUMENTS

| | | | |
|---|---|---|---|
| 3,683,389 A | 8/1972 | Hollis | |
| 3,723,644 A | 3/1973 | Haskell et al. | |

(Continued)

FOREIGN PATENT DOCUMENTS

| | | |
|---|---|---|
| DE | 2941363 | 10/1979 |
| DE | 2929429 | 2/1980 |

(Continued)

OTHER PUBLICATIONS

International Search Report for International Patent Application No. PCT/IL10/00972 dated Mar. 11, 2011.

(Continued)

*Primary Examiner* — Anhtuan T Nguyen
*Assistant Examiner* — Alexandra Newton
(74) *Attorney, Agent, or Firm* — Pearl Cohen Zedek Latzer Baratz LLP

(57) ABSTRACT

A method and device may control energy consumption of in an in vivo imaging device by determining or estimating an amount of energy needed to capture images at a frame rate until a complete passage of the device through a predetermined region of the gastrointestinal tract, and alter or limit the frame capture rate accordingly.

11 Claims, 3 Drawing Sheets

(56) References Cited

U.S. PATENT DOCUMENTS

| | | |
|---|---|---|
| 3,888,237 A | 6/1975 | Mori |
| 3,971,362 A | 7/1976 | Pope et al. |
| 4,149,769 A | 4/1979 | Zobel |
| 4,278,077 A | 7/1981 | Mizumoto |
| 4,523,227 A | 6/1985 | Hurst |
| 4,629,424 A | 12/1986 | Lauks et al. |
| 4,689,621 A | 8/1987 | Kleinberg |
| 4,741,327 A | 5/1988 | Yabe |
| 4,844,076 A | 7/1989 | Lesho et al. |
| 4,895,431 A | 1/1990 | Tsujiuchi et al. |
| 4,936,823 A | 6/1990 | Colvin et al. |
| 4,953,539 A | 9/1990 | Nakamura et al. |
| 5,098,426 A | 3/1992 | Sklar et al. |
| 5,179,607 A | 1/1993 | Sellers et al. |
| 5,209,220 A | 5/1993 | Hiyama et al. |
| 5,239,418 A | 8/1993 | Tyler et al. |
| 5,262,871 A | 11/1993 | Wilder et al. |
| 5,267,033 A | 11/1993 | Hoshino |
| 5,279,607 A | 1/1994 | Schentag et al. |
| RE34,965 E | 6/1995 | Sugiyama |
| 5,421,337 A | 6/1995 | Richards-Kortum et al. |
| 5,441,041 A | 8/1995 | Sauer et al. |
| 5,452,004 A | 9/1995 | Roberts |
| 5,477,858 A | 12/1995 | Norris et al. |
| 5,551,947 A | 9/1996 | Kaali |
| 5,569,292 A | 10/1996 | Scwemberger et al. |
| 5,572,252 A | 11/1996 | Naka et al. |
| 5,596,366 A | 1/1997 | Takashima et al. |
| 5,604,531 A | 2/1997 | Iddan et al. |
| 5,662,587 A | 9/1997 | Grundfest et al. |
| 5,666,955 A | 9/1997 | Kondo et al. |
| 5,681,260 A | 10/1997 | Ueda et al. |
| 5,697,384 A | 12/1997 | Miyawaki et al. |
| 5,748,232 A | 5/1998 | Konuma |
| 5,784,099 A | 7/1998 | Lippincott |
| 5,819,736 A | 10/1998 | Avny et al. |
| 5,833,603 A | 11/1998 | Kovacs et al. |
| 5,853,005 A | 12/1998 | Scanlon |
| 5,873,830 A | 2/1999 | Hossack et al. |
| 5,928,159 A | 7/1999 | Eggers et al. |
| 5,993,378 A | 11/1999 | Lemelson |
| 6,009,189 A | 12/1999 | Schack |
| 6,018,650 A | 1/2000 | Petsko et al. |
| 6,157,677 A | 12/2000 | Martens et al. |
| 6,162,171 A | 12/2000 | Ng et al. |
| 6,165,128 A | 12/2000 | Cespedes et al. |
| 6,172,712 B1 | 1/2001 | Beard |
| 6,228,030 B1 | 5/2001 | Urbano et al. |
| 6,240,312 B1 | 5/2001 | Alfano et al. |
| 6,248,469 B1 | 6/2001 | Formato et al. |
| 6,402,686 B1 | 6/2002 | Ouchi |
| 6,428,469 B1 | 8/2002 | Iddan et al. |
| 6,438,405 B1 | 8/2002 | Mooney et al. |
| 6,475,145 B1 | 11/2002 | Baylor |
| 6,493,466 B1 | 12/2002 | Honda et al. |
| 6,494,827 B1 | 12/2002 | Matsumoto et al. |
| 6,533,721 B1 | 3/2003 | Buetter et al. |
| 6,535,243 B1 | 3/2003 | Tullis |
| 6,546,276 B1 | 4/2003 | Zanelli |
| 6,587,711 B1 | 7/2003 | Alfano et al. |
| 6,603,981 B1 | 8/2003 | Carillo, Jr. et al. |
| 6,632,175 B1 | 10/2003 | Marshall |
| 6,635,834 B1 | 10/2003 | Wenner |
| 6,709,387 B1 | 3/2004 | Glukhovsky et al. |
| 6,719,684 B2 | 4/2004 | Kim et al. |
| 6,738,265 B1 | 5/2004 | Svarfvar et al. |
| 6,744,974 B2 | 6/2004 | Neuman |
| 6,764,440 B2 | 7/2004 | Iddan et al. |
| 6,934,573 B1 | 8/2005 | Glukhovsky et al. |
| 7,009,634 B2 | 3/2006 | Iddan et al. |
| 7,022,067 B2 | 4/2006 | Glukhovsky et al. |
| 7,061,523 B2 | 6/2006 | Fujita et al. |
| 7,083,578 B2 | 8/2006 | Lewkowicz et al. |
| 7,104,952 B2 | 9/2006 | Iddan et al. |
| 7,112,752 B1 | 9/2006 | Wenner |
| 7,160,258 B2 | 1/2007 | Imran et al. |
| 7,251,383 B2 | 7/2007 | Iddan |
| 7,561,908 B2 | 7/2009 | Glukhovsky et al. |
| 7,970,455 B2 | 6/2011 | Zilberstein et al. |
| 8,159,549 B2 | 4/2012 | Glukhovsky et al. |
| 2001/0031005 A1 | 10/2001 | Nister et al. |
| 2001/0035902 A1 | 11/2001 | Iddan et al. |
| 2001/0051766 A1 | 12/2001 | Gazdzinski |
| 2002/0010390 A1 | 1/2002 | Guice et al. |
| 2002/0032366 A1 | 3/2002 | Iddan et al. |
| 2002/0080881 A1 | 6/2002 | Honda et al. |
| 2002/0103417 A1 | 8/2002 | Gazdzinski |
| 2002/0132226 A1 | 9/2002 | Nair et al. |
| 2002/0191113 A1 | 12/2002 | Siefken |
| 2002/0198439 A1 | 12/2002 | Mizuno |
| 2002/0198470 A1 | 12/2002 | Imran et al. |
| 2003/0013370 A1 | 1/2003 | Glukhovsky |
| 2003/0069474 A1 | 4/2003 | Couvillon |
| 2003/0117491 A1 | 6/2003 | Avni et al. |
| 2003/0167000 A1 | 9/2003 | Mullick et al. |
| 2003/0208107 A1 | 11/2003 | Refael |
| 2004/0010375 A1 | 1/2004 | Schomacker et al. |
| 2004/0073087 A1 | 4/2004 | Glukhovsky et al. |
| 2004/0180391 A1 | 9/2004 | Gratzl et al. |
| 2005/0266074 A1 | 12/2005 | Zilberstein et al. |
| 2005/0281446 A1 | 12/2005 | Glukhovsky et al. |
| 2006/0069317 A1 | 3/2006 | Horn et al. |
| 2006/0178557 A1* | 8/2006 | Mintchev et al. .............. 600/104 |
| 2006/0184039 A1 | 8/2006 | Avni et al. |
| 2006/0195014 A1 | 8/2006 | Seibel et al. |
| 2007/0043258 A1 | 2/2007 | Sarwari |
| 2007/0066868 A1* | 3/2007 | Shikii ........................ 600/118 |
| 2007/0104272 A1 | 5/2007 | He et al. |
| 2007/0225560 A1 | 9/2007 | Avni et al. |
| 2007/0230893 A1 | 10/2007 | Meron et al. |
| 2007/0232887 A1 | 10/2007 | Khait et al. |
| 2007/0255098 A1 | 11/2007 | Wang et al. |
| 2008/0045789 A1* | 2/2008 | Sawachi ........................ 600/111 |
| 2008/0051642 A1 | 2/2008 | Krupnik |
| 2008/0147087 A1 | 6/2008 | Horn et al. |
| 2008/0177136 A1 | 7/2008 | Wang |
| 2008/0242931 A1 | 10/2008 | Nishino |
| 2008/0269664 A1 | 10/2008 | Trovato et al. |
| 2009/0076326 A1* | 3/2009 | Mitsuhashi et al. .......... 600/118 |
| 2009/0124874 A1 | 5/2009 | Gono et al. |
| 2009/0148058 A1 | 6/2009 | Dane et al. |
| 2009/0202117 A1 | 8/2009 | Vilarino et al. |
| 2009/0274347 A1 | 11/2009 | Gat et al. |
| 2009/0306632 A1 | 12/2009 | Trovato et al. |
| 2010/0110168 A1 | 5/2010 | Avni et al. |
| 2010/0220179 A1* | 9/2010 | Wang ............................. 348/68 |
| 2010/0271468 A1* | 10/2010 | Wang ............................. 348/77 |
| 2010/0324381 A1 | 12/2010 | Glukhovsky et al. |
| 2012/0200684 A1 | 8/2012 | Glukhovsky et al. |
| 2012/0271104 A1 | 10/2012 | Khait et al. |
| 2013/0211255 A1 | 8/2013 | Glukhovsky et al. |

FOREIGN PATENT DOCUMENTS

| | | |
|---|---|---|
| DE | 34 40 177 | 5/1986 |
| DE | 19723454 A1 | 12/1998 |
| EP | 0 667 115 | 8/1995 |
| EP | 0677272 A1 | 10/1995 |
| IL | 122602 | 4/2005 |
| JP | 49-114940 | 11/1974 |
| JP | 57-45833 | 3/1982 |
| JP | 4109927 | 4/1992 |
| JP | 1992-144533 | 5/1992 |
| JP | 4-180736 | 6/1992 |
| JP | 5015515 | 1/1993 |
| JP | 06-114037 | 4/1994 |
| JP | 07-111985 | 5/1995 |
| JP | 10136252 | 5/1998 |
| JP | 10-243286 | 9/1998 |
| JP | 2000-083182 | 3/2000 |
| JP | 2001-224553 | 8/2001 |
| JP | 3-289779 | 8/2003 |
| JP | 04022325 | 1/2004 |
| WO | WO 92/21307 | 12/1992 |

(56) References Cited

FOREIGN PATENT DOCUMENTS

| | | |
|---|---|---|
| WO | WO 94-11040 | 5/1994 |
| WO | WO 98/11816 | 3/1998 |
| WO | WO 99/22640 | 5/1999 |
| WO | WO 99/30610 | 6/1999 |
| WO | WO 00/22975 | 4/2000 |
| WO | WO 01/08548 | 2/2001 |
| WO | WO 01/50941 | 7/2001 |
| WO | WO 01/53792 | 7/2001 |
| WO | WO 01/65995 | 9/2001 |
| WO | WO 01/87377 | 11/2001 |
| WO | WO 02/26103 | 4/2002 |
| WO | WO 2006/059331 | 6/2006 |
| WO | WO2011/061746 | 5/2011 |

OTHER PUBLICATIONS

Office Action for U.S. Appl. No. 09/571,326 dated Oct. 3, 2002.
Supplementary Partial European Search Report for EP 01 92 9965 dated May 10, 2006.
International Search Report for International Application No. PCT/IL01/00427 dated Sep. 19, 2002.
Office Action for U.S. Appl. No. 10/705,982 dated Jun. 15, 2005.
Shedding light on cancer diagnosis—Powell (Ed.), May 2000, Laser Focus World.
The Radio Pill, Rowlands, et al., British Communications and Electronics, Aug. 1960, pp. 598-601.
Wireless transmission of a color television moving image from the stomach using a miniature CCD camera, light source and microwave transmitter. Swain CP, Gong F, Mills TN. Gastrointest Endosc 1997;45:AB40, vol. 45, No. 4, 1997.
BBC News Online—Pill camera to 'broadcast from the gut', Feb. 21, 2000, www.news.bbc.co.uk.
Estimating Motion in Image Sequences, Stiller et al., IEEE Signal Processing Magazine, Jul. 1999, pp. 70-91.
Shin-ichi et al., "Robots for the future". Nipponia 13, Nov. 29, 2001. www.rfnorkia.com-NORIKA3. Dec. 24, 2001.
Y. Bar-Cohen, Ed., "Electroactive Polymer Actuators as Artificial Muscles" SPIE Press, Bellingham, Washington; 2001.
Hannan et al., "'The Elephant Trunk' Manipulator, Design and Implementation", pp. 1-6.
Partial European Search Report of Application No. 08 01 7205 dated Oct. 28, 2008.
Office Action for European Patent Application No. 02795412 mailed Mar. 1, 2011.
Notice of Allowance for Japanese Patent Application No. 2000-538600 dated Jul. 17, 2008.
Office Action for Japanese Patent Application No. 2000-538600 dated Feb. 1, 2008.
Office Action for Japanese Patent Application No. 2000-538600 dated Dec. 17, 2007.
Office Action for Japanese Patent Application No. 2000-538600 dated May 14, 2007.
International Search Report of International Patent Application No. PCT/IL98/00608 dated May 20, 1999.
European Search Report for European Patent Application No. 98960065.5 dated Aug. 3, 2001.
Office Action for European Patent Application No. 98960065.5 dated Oct. 6, 2003.
Office Action for Canadian Patent Application No. 2,314,104 dated Apr. 10, 2006.
Office Action for Japanese Patent Application No. 2006-136080 dated Oct. 27, 2010.
Office Action for Japanese Patent Application No. 2006-136080 dated Apr. 25, 2011.
Office Action for U.S. Appl. No. 11/025,111 dated Jan. 28, 2008.
Office Action for U.S. Appl. No. 11/025,111 dated Oct. 30, 2008.
Office Action for U.S. Appl. No. 11/025,111 dated May 27, 2009.
Office Action for U.S. Appl. No. 11/025,111 dated Oct. 28, 2009.
Final Office Action for U.S. Appl. No. 11/025,111 dated May 26, 2010.
Office Action for U.S Appl. No. 11/025,111 dated Dec. 23, 2010.
Office Action for U.S. Appl. No. 13/424,684 dated Jun. 14, 2012.
Notice of Allowance for U.S. Appl. No. 09/581,628 dated Mar. 26, 2001.
Manual of Photogrammetry, Thompson (Ed.), vol. II, Third Edition, American Society of Photogrammetry 1966, pp. 812-813.
Lange et al., "Heidelberger Kapsel—Ein Kleinstsender Fuz Die pH-Messung im Magen", Telefunken-Zeitung, vol. 36, No. 5, pp. 265-270.
Yarbrough, III et al., "Evaluation of the Heidelberg pH Capsule: Method of Tubeless Gastric Analysis", The American Journal of Surgery, vol. 117, Feb. 1969, pp. 185-192.
Mackay, R. Stuart, "Bio-Medical Telemetry: Sensing and Transmitting Biological Information from Animals and Man", John Wiley and Sons, New York, 1970, pp. 244-245.
Office Action for U.S. Appl. No. 10/860,028 dated Nov. 16, 2005.
Office Action for U.S. Appl. No. 12/854,483 dated Nov. 28, 2011.
Office Action for U.S. Appl. No. 12/854,483 dated Apr. 8, 2011.
US Office Action for U.S. Appl. No. 10/200,548 dated Aug. 11, 2004.
US Notice of Allowance for U.S. Appl. No. 10/200,548 dated Mar. 11, 2005.
US Office Action for U.S. Appl. No. 11/140,291 dated Apr. 9, 2007.
US Office Action for U.S. Appl. No. 11/140,291 dated Jun. 23, 2008.
US Final Office Action for U.S. Appl. No. 11/140,291 dated Oct. 18, 2007.
US Final Office Action for U.S. Appl. No. 11/140,291 dated Jan. 8, 2008.
US Notice of Allowance for U.S. Appl. No. 11/140,291 dated Mar. 23, 2009.
U.S. Appl. No. 14/179,822, filed Feb. 20, 2014.
U.S. Appl. No. 13/208,611, filed Aug. 12, 2011.
Office Action of U.S. Appl. No. 13/208,611 dated Mar. 1, 2013.
Final Office Action of U.S. Appl. No. 13/208,611 dated Sep. 13, 2013.

* cited by examiner

SYSTEM AND METHOD FOR CONTROLLING POWER CONSUMPTION OF AN IN VIVO DEVICE

CROSS-REFERENCE TO RELATED APPLICATIONS

This application is a National Phase Application of PCT International Application No. PCT/IL2010/000972, International Filing Date Nov. 18, 2010, claiming priority of U.S. Patent Application 61/263,121, filed Nov. 20, 2009, which are hereby incorporated by reference in their entirety.

BACKGROUND OF THE INVENTION

Devices and methods for performing in vivo imaging of passages or cavities within a body are well known in the art. Such devices may include, inter alia, endoscopic imaging systems and devices, for example, an in vivo capsule, for performing imaging in various internal body cavities.

For it to be swallowable, an autonomous in vivo capsule must not exceed a certain girth and length, which in turn may limit the space available for the capsule components including its energy source. The limitation on the size of the energy source may translate into a limitation on the power available for the operation of the capsule.

The passage of an autonomous in vivo capsule through the peristalsis of the gastrointestinal (GI) tract may take several hours. A propelled capsule may complete the passage in a shorter time, but may require more energy to do it. Furthermore, the capsule may travel for several hours during the gastrointestinal tract before it reaches a region of interest, for example, the colon. It is important to ensure that upon reaching the region of interest, the capsule's energy source can provide sufficient energy for the operation of the capsule during the passage through the region of interest and at a desired rate of operation, such as a desired frame capture rate.

While traveling inside the body, the imaging device may capture images of, for example, surfaces of the intestine and may transfer the captured images at a fixed frame rate, continuously, to an image recorder outside the body to be analyzed by a physician. The device may move unevenly inside the passages or cavities of the body. For example, an in vivo capsule passing through a GI tract may be moving "slowly" in some part of the GI tract, and at some point of time and/or position may start to move "rapidly". If the in vivo device is capturing images at a fixed time interval, a physician performing diagnosis of the patient may receive fewer images for that part of the GI tract as a result of this sudden change in the movement of capsule.

Various methods may be used to control the rate of images being captured by the imaging device and/or transferred to a receiver or recorder. The imaging device may increase or decrease the rate of image capturing and the corresponding rate of frames being sent by the device.

However, when the rate of image capture and transmission is increased, so too is the power consumption. In some cases, variable transmission rates that are too high may deplete the power resources of the device. If the energy resources are depleted before the device is expelled from the body, regions of the GI tract may not be imaged.

SUMMARY

A method and device may control energy consumption of in an in vivo imaging device by determining or estimating an amount of energy needed to capture images at a frame rate until the passage of the device through a predetermined region of the GI tract, and alter or limit the frame capture rate accordingly.

BRIEF DESCRIPTION OF THE DRAWINGS

The invention will be understood and appreciated more fully from the following detailed description of various embodiments of the invention, taken in conjunction with the accompanying drawings of which.

Figure 1:
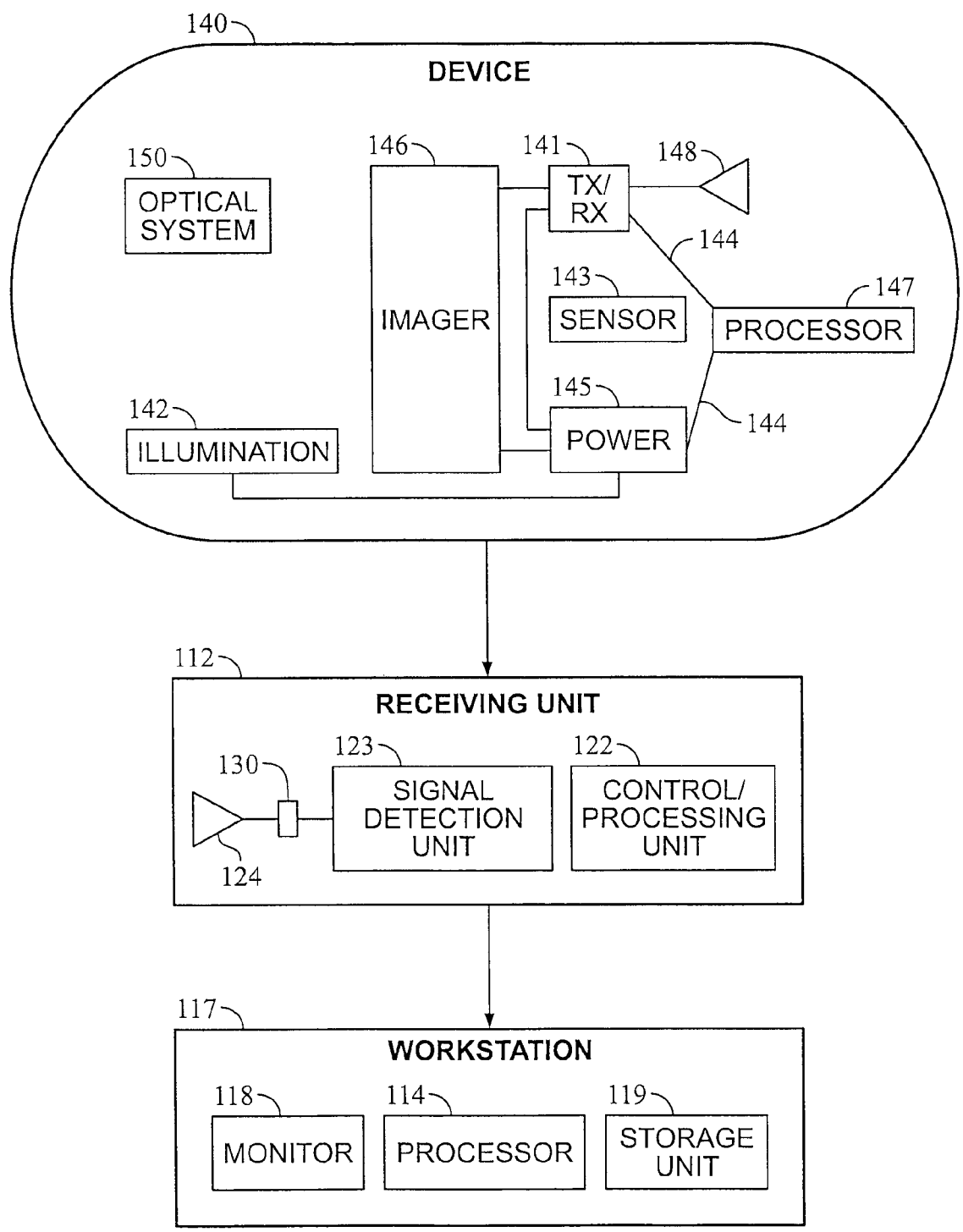
FIG. 1 is a schematic illustration of an in vivo imaging system according to one embodiment of the invention.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE INVENTION

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Some embodiments of the present invention are directed to an in vivo device that may be inserted into a body lumen, e.g., the GI tract, for example, from outside the body. Some embodiments are directed to a typically one time use or partially single use detection and/or analysis device. Some embodiments are directed to a typically swallowable in vivo device that may passively or actively progress through a body lumen, e.g., the GI tract, for example, pushed along by natural peristalsis or by magnetic or mechanic propulsion. Some embodiments are directed to in vivo sensing devices that may be passed through other body lumens, for example, through blood vessels, the reproductive tract, or the like. The in vivo device may be, for example, a sensing device, an imaging device, a diagnostic device, a detection device, an analysis device, a therapeutic device, or a combination thereof. In some embodiments, the in vivo device may include an image sensor or an imager and/or other suitable components. Some embodiments of the present invention may be directed to other imaging devices, not necessarily in vivo imaging.

Devices, systems and methods according to some embodiments of the present invention, including for example in vivo sensing devices, receiving systems and/or display systems, may be similar to embodiments described in U.S. Pat. No. 5,604,531 to Iddan et al., entitled "In vivo Video Camera System", and/or in U.S. Pat. No. 7,009,634 to Iddan et al., entitled "Device for In vivo Imaging", all of which are hereby incorporated by reference in their entirety. Devices, systems and methods according to some embodiments of the present invention, may be similar to or incorporate embodiments described in PCT Patent Application Publication Number WO2006059331, entitled "TWO-WAY COMMUNICATION IN AN AUTONOMOUS IN VIVO DEVICE", incorporated by reference herein in its entirety, which discloses an autonomous in vivo sensing device that includes an in vivo transceiver to both transmit wireless signals to for example an external receiver, and to receive wireless signals from for example an external transmitter. Devices, systems and methods according to some embodiments of the present invention, may be similar to the commercial PillCam® SB2 or Pill-Cam® Colon capsules and the associated data recorders and RAPID® workstation of the common assignee. The application further discloses that wireless signals received by the in vivo transceiver may be or may include command or control signals that may activate, de-activate or alter an operational state of one or more functions of the in vivo device. The wireless signals transmitted by the in vivo transceiver may be or include sensory data such as for example image data that may be collected by the in vivo sensing device.

Devices and systems as described herein may have other configurations and/or sets of components. For example, an external receiver/recorder unit, a processor and a monitor, e.g., in a workstation, such as those described in the above mentioned publications, may be suitable for use with some embodiments of the present invention. The present invention may be practiced using an endoscope, needle, stent, catheter, etc. Some in vivo devices may be capsule shaped, or may have other shapes, for example, a peanut shape or tubular, spherical, conical, or other suitable shapes.

Embodiments of the invention include a device and method for controlling energy consumption of in an in vivo imaging device (e.g., a swallowable capsule). A minimal amount of energy needed to operate the in vivo imaging device, e.g. capture image frames at a minimum non-zero frame rate until the complete passage of the device through at least a predetermined anatomical region of the GI tract and transmit the images to a receiving device, may be determined. A non-zero frame rate may include a fixed or variable non-zero frame capture rate. The non-zero rate may be determined according to several frame rate parameters such as speed of the imaging device, the organ or anatomical section or region of the body lumen which is being imaged, the motility of the body lumen, etc. The minimal frame rate may be predetermined, for example set to 4 frames per second or 48 frames per minute, or may be selected according to one or more frame rate parameters.

In some embodiments, the complete passage time of the device through at least a predetermined anatomical region of the GI tract may be estimated or calculated. For example, a maximum duration of the passage of the device through the entire length of the body passage to be imaged may be estimated. In one example, the complete passage time of the in vivo device through the body lumen anatomical region may be estimated as 10 hours for a colon imaging procedure, and 9 hours for a small bowel imaging procedure. In some embodiments, the complete passage time of the device through the anatomical region intended for imaging may be calculated on-the-fly based on image data or position data received from the in vivo imaging device. Other passage durations may be determined, for example tuned according to the patient's symptoms or suspected pathological condition. The complete passage time of the device through at least a predetermined anatomical region of the GI tract or the maximum duration of the passage of the device through the entire length may be pre-set or known beforehand. For example, a device or a system may have such values pre-set, and this pre-set value may control the determinations of the energy needed.

The "minimal" amount of energy may be the amount of energy needed (or estimated or calculated to be needed) to complete the in vivo imaging procedure through a path, and thus in some embodiments may be the maximum amount of energy needed (or estimated or calculated to be needed) to complete the task of capturing the images at a certain minimal frame rate. The minimal amount of energy required may include energy for one or more operations of the imaging device required for completing the imaging procedure through a body lumen, for example, energy required for capturing image frames, illuminating the illumination sources for capturing the images, transmitting the images to an external receiving device, and controlling the in vivo imaging device, and/or performing other functions. An operating frame rate may be determined that uses an amount of energy from the device power supply so that the available energy remaining in the device power supply is greater than or equal to the minimal amount of energy. The in vivo device may be caused to or controlled to capture images at a rate that is less than or equal to the operating frame rate.

Some embodiments of the present invention may include, for example, a swallowable in vivo device. In other embodiments, an in vivo device need not be swallowable and/or autonomous and may be remotely controllable or navigated, e.g., via magnets, and may have other shapes or configurations. Some embodiments may be used in various body lumens, for example, the GI tract, blood vessels, the urinary tract, the reproductive tract, or the like.

Embodiments of the in vivo device may be self-contained and may be autonomous or controllable (e.g., via magnetic maneuvering). For example, the in vivo device may be or may include a capsule or other unit where all the components are substantially contained within a container, housing or shell, and where the in vivo device does not require any wires or cables to, for example, receive power or transmit information. The in vivo device may communicate with an external receiving and display system to provide display of data, control, or other functions. For example, power may be provided by an internal battery or an internal energy or power source, or using a wired or wireless power-receiving system. Other embodiments may have other configurations and capabilities. For example, components may be distributed over multiple sites or units; and control information or other information may be received from an external source.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body. Other embodiments of the invention need not be used with in vivo imaging devices.

Embodiments of the present invention may describe a system and method for monitoring the device power and energy usage and controlling the frame capture rate based thereon to for example ensure a sufficient amount of useable energy is maintained to complete image capture by the device along a complete body passage (other embodiments need not complete the image capture along a complete passage). Capture along a complete body passage may include imaging the entire length of the GI tract, an anatomical sub-region of the GI tract, e.g., the small bowel or colon, a region ending near where the capsule is expelled from the body, or any other predetermined length or region of the body.

An imaging device may have a power source, such as, one or more batteries or power cells, with a limited or finite amount of available power. The available power may be depleted over time by the degrading of chemicals while the device is in storage. The available power may also be used to operate the device. For example, to capture each image frame, the device typically operates illumination sources, an imager, a transmitter or a transceiver, a processor, and/or other components, each of which uses power from the power source. For a given distance or time interval, as the frame rate increases, the number of frames captured per time unit increases and thus, the greater the amount of energy used per time unit to capture frames. The frame rate used by the device may increase, for example, based on an analysis of images, for example based on degree of similarity between sequential frames, detection of pathology in frames, the device's speed or a degree of acceleration and/or rotation. For example, when it is determined that the device is stationary, the frame rate may substantially decrease, and when movement is detected the frame rate may increase according to a detected degree of acceleration. The frame rate may increase when it is determined that the device has reached a segment or organ of interest. For example, in a colon imaging procedure, the frame rate may be lower while the device is capturing images in the stomach and the small bowel, and the frame rate may increase when the device passes the cecum. Similarly, the frame rate may decrease when the device is capturing images in areas which are of less importance for the current examination procedure. In conventional devices, the cumulative energy required to capture frames at the optimal frame rate may exceed the total available or useable energy of the power source, e.g., if the passage has a large degree of redness or bleeding causing the frame rate to increase. In such a case, the device power may be depleted quickly, and the device cannot continue to take images and may leave entire regions of the body passage undocumented.

Embodiments of the invention include limiting the frame rate so that the energy used to capture images does not deplete the energy needed to capture image frames until the device has captured the entire length of the desired passageway. For example, an energy reserve is maintained that ensures complete capture of the images along substantially the entire length of the body passage or the organ of interest in the procedure. As the device progresses through the body, less distance remains until the end, and less time, and thus fewer images are needed to complete image capture for the entirety of the passage. Thus, the energy reserve may decrease over time as the device passes through the body. In one embodiment, the energy reserve is calculated so that the device has sufficient energy to capture frames at no less than a predetermined minimal frame rate until the end of the body passage (or up until some desired point prior to the end). A value for the energy reserve may be continually or repeatedly calculated and updated so that at any given point along the passage, the target reserve allows for the capture frames at no less than a predetermined minimal frame rate until the end of the body passage (or up until some point prior to the end) from that point on.

A processor (e.g., in a workstation, receiving unit or the in vivo device) may monitor the energy usage of the device, e.g., for each frame, to determine if a higher than minimum frame rate would deplete the energy reserve. In this way, optimal frame rates are checked and adjusted to ensure the power source maintains a sufficient amount of power to complete image capture along the entire length of the body passage, or up until some desired point prior to the end. If the higher frame rate would deplete energy resources, the processor may set the device to a minimum frame rate mode, e.g., to capture frames at a rate that maintains the energy reserve, and the device may capture and/or transmit images at this rate. If the higher frame rate would not deplete energy resources, the higher frame rate is allowable and the device may be set to a higher frame rate mode. In some embodiments, although the higher frame rate is allowable, the higher frame rate need not be used. The processor may use an optimization mechanism to determine, from among the allowable frame capture rates, which frame rate is optimal.

The processor may calculate an optimal frame rate from among the allowable frame capture rates, for example, based on any individual or combination of parameters. In some embodiments, an optimal frame rate may be determined, for example, based on the motion, speed, acceleration, location, color of images (e.g., the rate increasing as the amount of redness increases indicating blood), differences in color, texture or patterns between sequential images, image recognition, impedance variation, etc. As the sensed values for these parameters change through a body cavity, the device may toggle or switch back and forth among the allowable frame capture rates. If the optimal frame rate is less than or equal to the allowable frame rates (e.g., if it still preserves the energy reserve), an imager may capture one or more subsequent frames at the optimal frame rate. If the optimal frame rate greater than the allowable frame rates (e.g., if it would deplete the energy reserve), an imager may capture one or more frames at the greatest allowable frame rate.

A frame rate or capture frame rate may refer to a non-zero rate at which images or frames are captured by the device and therefore excludes operational modes in which the device is not collecting images (e.g. a standby mode), has no power, or is in an off mode.

Embodiments of the invention may include a reduced power or dormant mode for the device in which the device may temporarily stop capturing images or may capture images at a rate less than the predetermined minimum capture rate. In the reduced power or dormant mode, the device will progress along the passageway and less distance of the passageway may need to be imaged when the device resumes normal power operations. Accordingly, after the power reduction, fewer total images of the passageway may need to be taken in order to maintain the predetermined minimum capture rate. The minimum energy reserve may be recalculated after each power reduction to have a smaller value (for taking fewer total images) than previous calculations. In one embodiment, when the remaining available energy in the device is approximately equal to the minimum energy reserve (e.g., the device may only capture images at the predetermined minimum capture rate for the remainder of the passage), the device may automatically or in response to the passage of time or a detection of an in vivo condition, such as a change of organ, or a combination of these factors, enter a reduced power or dormant mode. The minimum energy reserve may then be recalibrating to a smaller value than before the power reduction, and the device may once again have energy available to image at a capture rate that is higher than the predetermined minimum capture rate.

Embodiments of the invention may also include changing the transmission strength of the device, e.g., to a substantially minimum transmission strength to achieve sufficient signal clarity at an external receiving device. For example, when the in vivo device moves closer to an external receiver antenna, less signal strength may be needed to maintain a base level of signal clarity at the receiver. A feedback loop between an in vivo device transmitter and a device positioning system and/or an external device receiver may be used for the in vivo device to continuously or periodically (e.g., in time or for each frame) change the strength of the transmitted signals to meet the minimum transmission signal strength requirements.

Reference is made to FIG. 1, which schematically illustrates an in vivo system in accordance with some embodiments of the present invention. One or more components of the system may be used in conjunction with, or may be operatively associated with, the devices and/or components described herein or other in vivo devices in accordance with embodiments of the invention.

In some embodiments, the system may include a device 140 having a sensor, e.g., an imager 146, one or more illumination sources 142, a power source 145, and a transceiver 141. In some embodiments, device 140 may be implemented using a swallowable capsule, but other sorts of devices or suitable implementations may be used.

Receiver/recorder 112 may include a transceiver 130 to communicate with device 140, e.g., to periodically send a frame rate to device 140 and to periodically receive image, telemetry and energy usage data from device 140. Receiver/recorder 112 may in some embodiments is a portable device worn on or carried by the patient, but in other embodiments may be for example combined with workstation 117. A workstation 117 (e.g., a computer or a computing platform) may include a storage unit 119 (which may be or include for example one or more of a memory, a database, etc. or other storage systems), a processor 114, and a monitor 118.

Transceiver 141 may operate using radio waves; but in some embodiments, such as those where device 140 is or is included within an endoscope, transceiver 141 may transmit/receive data via, for example, wire, optical fiber and/or other suitable methods. Other known wireless methods of transmission may be used. Transceiver 141 may include, for example, a transmitter module or sub-unit and a receiver module or sub-unit, or an integrated transceiver or transmitter-receiver. In one embodiment, transceiver 141 includes at least a modulator for receiving an image signal from the sensor 146, a radio frequency (RF) amplifier, an impedance matcher and an antenna 148. The modulator converts the input image signal having a cutoff frequency $f_0$ of less than 5 MHz to an RF signal having a carrier frequency $f_r$, typically in the range of 1 GHz. While in one embodiment, the signal is an analog signal, the modulating signal may be digital rather than analog. The carrier frequency may be in other bands, e.g., a 400 MHz band. The modulated RF signal has a bandwidth of $f_r$. The impedance matcher may match the impedance of the circuit to that of the antenna. Other transceivers or arrangements of transceiver components may be used. For example, alternate embodiments may not include a matched antenna or may include a transceiver without a matching circuit. In alternate embodiments, device 140 may have different configurations and include other sets of components. Other frequencies may be used. In yet further embodiments, sensors other than image sensors may be used, such as pH meters, temperature sensors, pressure sensors, etc. and input RF signals other than image signals may be used.

Transceiver 141 may send different types of signals, including for example telemetry signals, image signals and beacon signals. Other types of signals may be transmitted by transceiver 141. Information sent from device 140 may include information sensed by sensors in the device such as images, pH, temperature, location and pressure. Information sent from device 140 may include telemetry information, regarding the capsule ID, time counter, image type data and the status of components in the device, such as current image capturing mode or frame rate of the imager, different allowable frame rates, power usage for capturing each individual image frame or a group of image frames, power usage for each allowable frame rate, remaining power of the device power source, amount of energy reserve needed to capture image frames until complete passage of the device through a body passage at a minimal frame rate. The signals may be sent separately or as part as a larger frame, for example a frame including both telemetry-type and image-type signals.

Embodiments of device 140 may be autonomous and self-contained or may be controllable capsules (e.g., magnetically maneuvered). For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may include an in vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 may be operationally connected to transmitter or transceiver 141. Transceiver 141 may transmit images to, for example, external transceiver or receiver/recorder 112 (e.g., through one or more antennas), which may send the data to workstation 117, processor 114 and/or to storage unit 119. Transceiver 141 may also include control capability, although control capability may be included in a separate component, e.g., processor 147. Transceiver 141 may include any suitable transmitter able to transmit image data, other sensed data, and/or other data (e.g., control data, beacon signal, etc.) to a receiving device. Transceiver 141 may also be capable of receiving signals/commands, for example from an external transceiver. For example, in some embodiments, transceiver 141 may include an ultra low power Radio Frequency (RF) high bandwidth transmitter, possibly provided in Chip Scale Package (CSP).

In some embodiments, transceiver 141 may transmit/receive via antenna 148. Transceiver 141 and/or another unit in device 140, e.g., a controller or processor 147, may include control capability, for example, one or more control modules, processing module, circuitry and/or functionality for controlling device 140, for controlling the frame capture rate or settings of device 140, and/or for performing control operations or processing operations within device 140. According to some embodiments, transceiver 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like, such as ENERGIZER® LONG LIFE BATTERY 1.55V, 5 mA, product number 399 or ENERGIZER® SILVER OXIDE BATTERY 1.55V, product number 370. Other suitable power sources may be used. For example, power source 145 may receive power or energy from an external power source (e.g., an electromagnetic field generator), which may be used to transmit power or energy to in vivo device 140. Typically, power source 145 may have an initial amount of energy to be used during the imaging procedure, and additional energy may not be obtained or harvested during the procedure.

Power source 145 may be internal to device 140, and/or may not require coupling to an external power source, e.g., to receive power. Power source 145 may provide power to one or more components of device 140 continuously, substantially continuously, or in a non-discrete manner or timing, or in a periodic manner such as each time a frame is captured, an intermittent manner, or an otherwise non-continuous manner. In some embodiments, power source 145 may provide power to one or more components of device 140, for example, not necessarily upon-demand, or not necessarily upon a triggering event or an external activation or external excitement.

Power source 145 may be operationally coupled to a data bus 144, and may provide data regarding the status of different battery parameters, for example upon request. The battery data parameters that may be read from the battery may include the estimated time left to operate in at a specific capture rate or device mode (or energy remaining, which may be used to computer such a time-left value), current capacity, voltage, battery and/or manufacturer identification codes, maximum error percentage of the capacity, etc. In one embodiment, device 140 may periodically transmit the instantaneous energy, e.g., used for capturing each image frame, used since the last transmission, used for each operation or a group of operations, etc. The amount of energy remaining in power source 145 may be determined after every image frame and/or device 140 transmission, or at other times. The amount of energy remaining in power source 145 may be determined, for example, by subtracting the sum of the instantaneous energy values transmitted by device 140 (e.g., giving the current total energy usage) from the available energy supply of power source 145. The frame rate at any point in time may be calculated and controlled to ensure that the amount of energy remaining in power source 145 is greater than or equal to the amount of energy reserve needed to capture image frames at a minimum frame rate until the complete passage of device 140. Other methods of estimating the energy or capacity remaining in the battery may be used. A specific signal, separate from power provided by the battery during normal use, need not be used.

Transceiver 141 may include a processing unit, processor or controller, for example, to process signals and/or data generated by imager 146. In another embodiment, the processing unit may be implemented using a separate component within device 140, e.g., controller or processor 147, or may be implemented as an integral part of imager 146, transceiver 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transceiver 141, and may be implemented, for example, using an ASIC.

In some embodiments, imager 146 may acquire in vivo images in a discrete or periodic manner, or in an intermittent manner, or an otherwise non-continuous manner, for example, at an interval according to a variable one of a plurality of frame capture rates. The capture rate may be different for each frame and may be calculated with respect to the most recent previous captured image or group of images. The frame capture rate may be adjusted at any point in time to an optimal rate, e.g., sufficient to see detail during periods of fast motion of the device or in "important" regions, where capturing images at that rate uses less than or equal to an amount of energy available in order to maintain an energy reserve to capture frames at a minimal frame rate for the remainder of the body passage.

An imaging or image capturing procedure may include the time period during which the imager 146 is capturing images and the transceiver 141 is transmitting the image data to the receiving unit 112. Commands may be received by the device 140 from an external control unit which may be a separate unit located outside of the patient's body or may be integrated, for example with the receiving unit 112. The external control unit may be, for example, the control/processing unit 122 integrated within receiving unit 112. In one embodiment, the device power source 145 may transmit an indication through transceiver 141, notifying the control/processing unit 122 of a low battery status. The imaging device processor 147, or another unit operatively connected to the battery, may sample internal registers in the battery to determine, for example, the current battery status, or other battery parameters. Control/processing unit 122 may, in response, transmit a control command to device 140 to decrease the frame capture rate to a greater than zero value. The transmission power may be controlled in real time or preprogrammed, for example per signal type or according to the calculated remaining amount of energy in device 140. Other methods of determining battery power may be used; for example a unit such as processor 147 or transmitter 141 may sample the battery periodically to determine power characteristics such as the remaining voltage level, the estimated amount of time left according to current usage, etc.

In some embodiments, device 140 may include one or more illumination sources 142, for example one or more Light Emitting Diodes (LEDs), "white LEDs", or other suitable light sources, such as Nichia's LED product number NESW007BT or Nichia's product number NESW007AT B3/B5. Illumination sources 142 may, for example, illuminate a body lumen or cavity being imaged and/or sensed. An optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminating light, and/or performing other light processing operations.

In some embodiments, the components of device 140 may be enclosed within a housing or shell, e.g., capsule-shaped, oval, or having other suitable shapes. The housing or shell may be substantially transparent, and/or may include one or more portions, windows or domes that may be substantially transparent. For example, one or more illumination source(s) 142 within device 140 may illuminate a body lumen through a transparent, window or dome; and light reflected from the body lumen may enter the device 140, for example, through the same transparent or portion, window or dome, or, optionally, through another transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

According to one embodiment, while device 140 traverses a patient's GI tract, the device 140 transmits image and possibly other data to components located outside the patient's body, which receive and process the data. Typically, receiving unit 112 is located outside the patient's body in one or more locations. The receiving unit 112 may typically include, or be operatively associated with, for example, one or more antennas, sensors, or an antenna array 124, for receiving and/or transmitting signals from/to device 140. Receiving unit 112 typically includes an image receiver storage unit. According to one embodiment, the image receiver 112 and image receiver storage unit are small and portable, and are typically worn on the patient's body (or located in close proximity to the patient's body) during recording of the images.

The receiving unit 112 may include, or be operatively associated with a signal detection unit 123, which may detect signals transmitted from, for example, device 140. The signal detection unit 123 may be coupled or included in the antenna or antenna array 124.

The control/processing unit 122, processor 114 and/or processor 147 may evaluate the transmitted data including available energy in power source 145, and, for example, based on the information, may determine an image capture rate that ensures continued imaging along the entire passageway or the organ of interest, using at least a minimum capture rate.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

Processor 114 and processor 122 may include processing units, processors or controllers. The processing units may include, for example, a CPU, a DSP, a microprocessor, a controller, a chip, a microchip, a controller, circuitry, an IC, an ASIC, or any other suitable multi-purpose or specific processor, controller, circuitry or circuit.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image at one of a plurality, e.g., three, four, ten or a hundred, different frame capture rates, and may transmit the image data to the external receiving unit 112. Other constant and/or variable capture rates and/or transmission rates may be used.

While passively moving along the GI tract of a body, device 140 may acquire images at a variable acquisition rate. Device 140 may have an initial or default image capture rate of, e.g., four frames per second (4 Hz). During the operation of device 140, the frame rate may be adjusted, changed or controlled, for example, based on the power usage of the device, e.g., via a control or adjustment signals sent to device 140 by receiving unit 112. The frame capture rate may be calculated externally to device 140, e.g., by processor 114 of workstation 117) and transmitted from transceivers 130 and/or workstation 117 and received by transceivers 141 of device 140. Alternatively, the frame capture rate may be calculated internally to device 140, e.g., by processor 147. The frame capture rate may be applied by processor 147 so that imager 146 may capture images at the received frame capture rate. For example, processor 114 and/or processor 147 may monitor power levels and determine and activate the corresponding frame capture rate based thereon. In one embodiment, processor 114 may determine an optimal capture rate, for example, based on device 140 parameters such as speed, motion, location, environment, and then adjust the capture rate, if necessary or other parameters (such as light control, light gain, length of light pulse, transmission strength and type of signal transmitted), to enable imaging along the full passageway or sufficiently to completely cover the organ or region of interest. Accordingly, processor 114 may set the frame capture rate of device 140 to be the rate that enables imaging along the full passageway that is closest to the optimal capture rate.

In one embodiment, processor 114 may monitor device 140 energy usage to determine, e.g., for each frame (or at longer intervals), if a higher than minimum frame rate would deplete the energy reserve. If not, the higher frame rate is allowable and device 140 may be set to a higher frame rate mode. However, although the higher frame rate is allowable, the higher frame rate need not be used. Processor 114 may use an optimization mechanism to determine, from among the allowable frame capture rates, which frame rate is optimal, taking into consideration parameters such as the current location of device 140, the speed of device 140 and/or other information extracted from the data received from device 140.

To determine the energy usage of device 140, processor 114 may determine the frame capture rate and an amount of energy associated with capturing a frame at each capture rate. In one embodiment, processor 114 may deduce the capture rate from the rate at which the frames are transmitted and/or received or may separately receive capture rate signals indicating the rates, e.g., which may be transmitted each time a frame is captured, periodically, together with or separately from the image data. Processor 114 may determine the overall energy usage of device 140 by summing the products of the number of frames captured at each capture rate and the energy associated with capturing a frame at that rate.

The optimal frame rate may be determined, for example, based on parameter(s) such as, motion, speed, acceleration, location, color of images (e.g., the rate increasing as the amount of redness increases indicating blood), differences in color, hue, saturation, texture or patterns between sequential images, impedance variation, degree of similarity when comparing sequential images, environmental pH values, etc. In one embodiment, optimal frame rate may be determined, for example, based on the region where the device is located within the body. For example, when a physician intends to investigate a region of interest in the body, such as the small bowel or colon, the optimal frame rate may be increased when the device is located in (or determined to be located in) that region or at a time when the device is expected to be located in that region. For example when investigating the colon, a relatively low or minimum frame rate may be used in the stomach, a frame rate intermediate to the relatively low and a relatively high rate may be used in the small bowel, and a relatively high or maximum frame rate may be used in the colon, although other combinations of rates may be used. In some embodiments, optimal frame rates associated with each range of parameter values may be pre-set and may be stored in a look-up table accessible by the device. In some embodiments, the pre-set values may be adjusted by sending command signals, for example from the receiver 112 to update the values or write new values which may be stored in device 140.

In one embodiment of the invention, a processor (e.g., processor 122, 114, and/or 147) may calculate an optimal frame rate, for example, based on a region where the device is located within the body. The region where the device is located may be determined, e.g., automatically or manually, for example, based on image differentiation, known colors (hue, saturation, pixel values), image parameters (intensity of images, gain and exposure parameters used in the image), textures, patterns, or in vivo objects (such as a lumen hole, villi, wrinkles, etc.) associated with each region. Alternatively or additionally, the region where the device is located may be determined using time-based parameters, e.g., by comparing the duration of capsule passage to predetermined times associated with each region (E.g., device 140 may stay in the stomach for up to 2 hours, traverse the small bowel in 4-6 hours, then stay in the colon up to, for example, 24 hours. These time averages may be, for example, based on typical small bowel procedures, using a specific preparation and examination diet regimen, and may be significantly different from times in a colon procedure). Alternatively or additionally, the region where the device is located may be determined using pH values known to be associated with each region of the body passage and/or using knowledge of structures in the GI tract (e.g. device 140 which has moved from the stomach to the small bowel will not likely return to the stomach). A combination of the above methods may be used.

Embodiments of the invention for determining the region where the device is located may be used, as described in U.S. Patent Application Publication No. 2009/0202117 to Vilarino et al., entitled "DEVICE, SYSTEM AND METHOD FOR MEASUREMENT AND ANALYSIS OF CONTRACTILE ACTIVITY" and U.S. Patent Application Publication No. 2006/0069317 to Horn et al., entitled "SYSTEM AND METHOD TO DETECT A TRANSITION IN AN IMAGE STREAM," all of which are hereby incorporated by reference in their entirety.

In one embodiment, a predetermined number (e.g., three) of different non-zero frame rates or ranges of frame rates may be used to capture frames respectively associated with (e.g., three) different body regions. For example, a relatively high frame rate or (HFR) of, e.g., 30-100 frames per second, may be used to capture frames in the colon, a relatively lower or medium frame rate (MFR) of, e.g., 10-20 frames per second, may be used to capture frames in the small bowel, and an even lower or lowest frame rate or (LFR) of, e.g., 1-5 frames per second, may be used to capture frames when the device is not in the colon or the small bowel, e.g., in the esophagus or stomach. Within each region of the body a range of higher frame rate to a lower frame rate are allowable. From among the range of allowable frame rates, processor 114 may determine, individually and instantaneously for each frame, the optimal frame rate. As parameter values in the body change (e.g., for speed, color, texture, presence of villi), the optimal frame rate also changes and therefore, device 140 may toggle back and forth between higher and lower frame rates. For example, in the colon and the small bowel, the capture rates toggles back and forth between a higher and lower frame rate. Different region or times of operation may have associated therewith different "higher" frame rates (e.g., of 36 or 35 frames per second in the colon and 20 frames per second in the small bowel). For example, in the colon, device 140 toggles between the colon HFR (e.g., of 36 or 35 frames per second) and the lower frame rates (e.g., of 4 frames per second), while in the small bowel, device 140 toggles between the small bowel MFR (e.g., of 20 frames per second) and the lower frame rates (e.g., of 4 frames per second).

In one embodiment, each different capture rate may be activated for a predetermined time during which device 140 is estimated to pass through each region. For example, device 140 may capture frames at the small bowel capture rate for, e.g., 1200 seconds or twenty minutes initiated by detecting the entrance to the small bowel, device 140 may capture at the colon capture rate for the following e.g., 10800 seconds or 180 minutes, device 140 may capture again at the small bowel capture rate for, e.g., 1800 seconds or thirty minutes, and device 140 may capture at the lowest or default capture rate for, e.g., until power source 145 is depleted of power or until the procedure is otherwise determined to be terminated.

Other regions, sub-regions, or frame rates may be used. For example, for a device directed to investigate the small bowel, the capture rate or the range of capture rates for the small bowel may be greater than the capture rate for the colon. In yet another embodiment, the capture rates or the range of capture rates of the small bowel and colon may be equal.

Once an optimal frame rate is calculated, the processor (e.g., processor 122, 114, and/or 147) may determine if capturing frames at the optimal frame rate would deplete the energy reserve needed to capture image frames until the completion of the device passage. If so, the optimal capture rate may be adjusted, e.g., as described in further detail in reference to FIG. 2.

Figure 2:
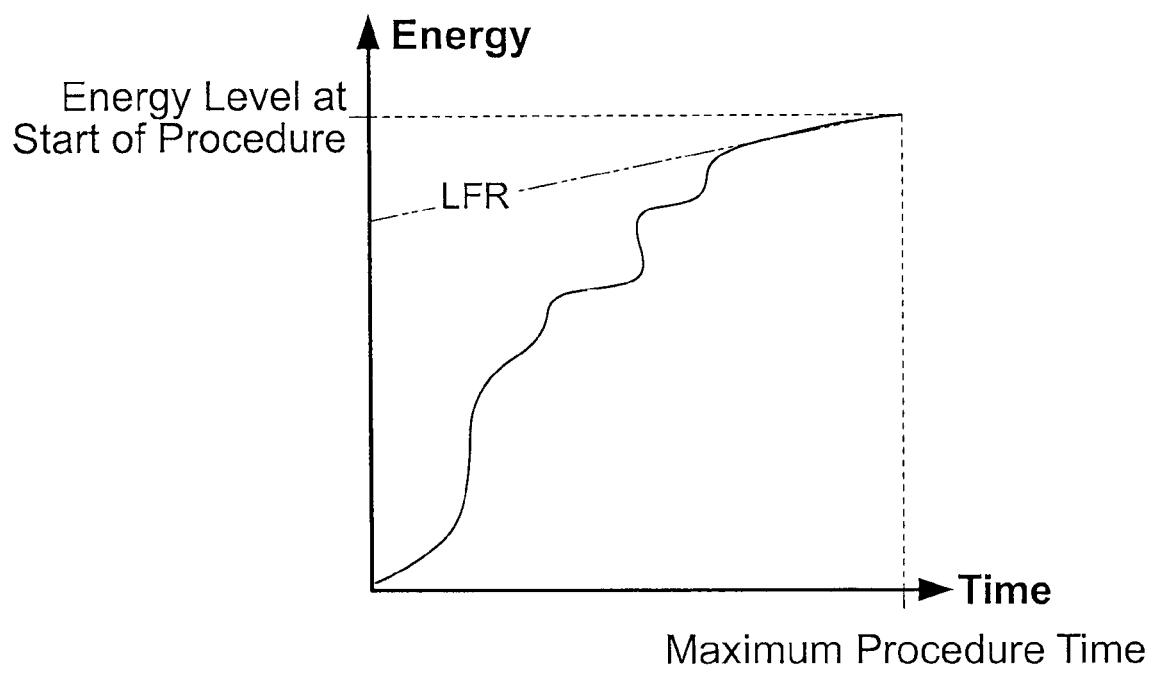
FIG. 2 is a graph of cumulative energy usage over time according to one embodiment of the invention.

Reference is made to FIG. 2, which is a graph of the cumulative energy usage over time in accordance with some embodiments of the present invention. The x-axis represents the passage of time, e.g., measured by a clock in processor 147 (e.g., a 8.1 MHz clock), from the beginning of image capturing or from the beginning of the imaging procedure to the estimated maximum duration of the passage of the device through the entire length of the body passage to be imaged, which may be predetermined or calculated during the procedure. The y-axis represents the cumulative energy levels over time with the upper horizontal line representing the energy level of the power source at the beginning of image capturing. The curved line indicates device energy usage over time. At any time along the x-axis, the energy difference between the curve and the x-axis represents the total energy used up to that time and the energy difference between the curve and the upper horizontal line represents the total energy still available for use in the power source. Over time as images are captured along the body passageway, the energy used increases and the available energy decreases, e.g., monotonically. As the slope along the curve increases, the frame rate increases and as the slope along the curve decreases, the frame rate decreases. A constant frame rate is indicated by a line with constant slope.

At any time along the x-axis, there is a minimum energy reserve in power supply 145 that remains unused to ensure that it is available to capture frames (e.g., at a minimum or least frame rate (LFR)) until the end of the body passage. In this description, the LFR is 4 frames per second and the energy above the LFR curve is the energy that is estimated to be needed to capture images at the LRF frame rate from that time until the end of the passageway or the region of interest. The minimum energy reserve is indicated by the difference between a curve labeled "LFR" and the upper horizontal line. Over time as device 140 passes through the body, fewer images are needed to complete the capture of the passageway. Thus, the minimum energy reserve may decrease, e.g., linearly, over time as device 140 passes through the body.

In order to ensure image capture at a minimum or least frame rate until the end of the body passage, the energy usage of device 140 should not deplete the minimum energy reserve of power supply 145, and at the relevant time along the x-axis the actual energy left in the power source should be at least the minimum energy reserve for that time. Thus, the LRF curve may represent the limit of the cumulative energy usage by device 140 at any time. Accordingly, the energy available in power source 145 (i.e., the energy above the energy usage curve) may be greater than or equal to this minimum energy reserve (i.e., the energy above the LFR curve). That is, in the graph, the energy usage curve and the LRF curve should never cross, but may asymptotically converge. When the energy available in power source 145 is greater than the minimum energy reserve, a greater than minimum capture rate may be used. However, once the energy available in the power source is equal to this minimum energy reserve (i.e., the curves converge), a minimum or least frame rate may be used until the power source 145 is fully depleted and device 140 reaches the end of the body passage.

In some embodiments, device 140 may allocate a predetermined portion of the total energy of power source 145 for each region of the body passage or time interval. For example, each region may have a separate maximal energy limit demarcated by respective minimal energy curves, which limit the energy use individually in each body region. In one embodiment, if device 140 is designed to investigate the colon, a greater amount of energy may be designated to the colon than the small bowel. Accordingly, the minimum energy LFR curve for the small bowel may have a relatively small distance between the curve and the x-axis as compared to the minimum energy LFR curve for the colon which may have a relatively large distance between the LFR curve for the colon and the LFR curve for the small bowel. Accordingly, when device 140 is passing through the small bowel, the energy usage may soon approach the energy limit and the frame rate may quickly decrease to the minimum frame rate. In contrast, a higher frame rate may be used for a longer period of time in the colon to which more energy is designated.

In another embodiment, different minimum or least frame rates may be designated for different regions in the body of time intervals. For example, if device 140 is designed to investigate the colon, the colon may have a least frame rate (e.g., 6 frames per second) that is greater than the least frame rate of the small bowel (e.g., 4 frames per second). In the graph, the minimum energy curve for the colon may appear at a greater incline than the minimum energy curve for the small bowel.

In one example depicted in Table 1 below, a plurality of different modes 0-4 are shown, each having a different non-zero frame rate for device 140. The amount of energy used to capture and transmit each frame may vary based on changing parameters during device 140 operation including, for example, energy used by transmitter 141 in which the strength of transmissions necessary for proper reception by receiving unit 112 may vary, e.g., based on the distance between device 140 and receiving unit 112, automatic light control which may vary, e.g., based on the light needed to properly illuminate an area for each specific frame, energy used by processor 147 and imager 146 which may vary, e.g., based on complexity or volume of image data, etc. Table 1 lists averages of the amount of energy used by device 140 for each frame in each mode as measured in laboratory testing.

TABLE 1

| Mode Number | Frame Rate [fr/sec] | Energy used per frame [mAh] $EngSt_i = CCC/BUC*T_{cycle}$ |
|---|---|---|
| 0 (Screening) | 4 | 3.298/0.75*(1/4/3600) = 1.0993/3600 |
| 1 (Pre-colon) | 0.8 | 0.458/0.95*(1/0.8/3600) = 0.6026/3600 |
| 2 (LFR) | 4 | 3.298/0.75*(1/4/3600) = 1.0993/3600 |
| 3 (HFR) | 36 | 9.704/0.5*(1/36/3600) = 0.5391/3600 |
| 4 (MFR) | 20 | |

The approximation of the energy used in each mode may be the average energy used to capture a single frame in each mode (e.g., measured and transmitted by device 140) multiplied by the total number of frames captured in that mode. In order to calculate the remaining amount of energy left in the device, the average values of different parameters are used, e.g. the energy used by the transmitter for transmission of an average frame, the average energy used by the imager for capturing a single frame, the average energy used by the imager for processing of an average frame, the average energy used by the illumination units to illuminate a frame and the mode of illumination used (for example, with pre-flash, pre-charge or without), and the average energy used for a capsule cycle and pause cycle. The calculation (or approximation) of the total energy used may include the sum of the average energies used in each mode. Accordingly, the total energy used at any time is:

$$UsedEnergyTillNow = \sum_i EngSt_i * Counter_i.$$

Additionally, energy for functions other than imaging (e.g., magnetic or mechanical propulsion or navigation, non-image sensors, therapeutic applications such as drug delivery, immobilization, etc.) may also be added to calculate the total energy used by device 140.

In one embodiment of the invention, the frame capture rates may be defined, for example, to satisfy the following equation:

$$BatteryFullCap - StorageEnergyReduction - UsedEnergyTillNow - \\ (ProcedureMaxTime - currentTime) * \frac{EngSt_{LFR}}{T_{LFR}} \leq 0 \quad \text{Eq(1)}$$

Parameters in the equation (1) may be defined, for example, as follows:
  BatteryFullCap may be the initial total energy supply of power supply 145. In one example, the initial energy may have a value of, for example, 52 mAh.
  StorageEnergyReduction may be the energy reduction due to storage conditions. For example, the storage conditions may be in 40° C. for up to 12 months. The energy reduction due to storage conditions may be an average value based on an estimation of storage conditions, e.g., including the amount of time power source 145 has been unused and the estimated storage temperature ranges during this time. The storage time may be calculated based on an assembly date recorded in device 140. The storage temperature may be estimated based on the storage facility and may be programmed into device 140, receiving unit 112 or workstation 117. If there is a range or uncertainty in the energy reduction due to storage conditions, a maximum, average, or minimum estimated value may be used.

StorageEnergyReduction=(BSDF+COMC)*Period [months] where BSDF is the battery self discharge factor and COMC is the energy depletion over time or the capsule off current monthly consumption.

UsedEnergyTillNow may be the total energy usage of device 140 accumulated until the current time.

$EngSt_i$ may be the average energy used to capture each frame, e.g., including illuminating, imaging, processing, and transmitting for each frame, in a mode "i," for example, where i=0-4 as defined in Table 1.

ProcedureMaxTime may be the maximum estimated time (e.g., in hours) for device 140 to completely pass through a pre-designated body passage, and may be predetermined, or calculated for example updated periodically using a feedback loop based on the current speed or path length traveled by device 140. In some embodiments, ProcedureMaxTime may be a preset value, for example equal to 9 or 10 hours, which may be determined, for example empirically, based on a typical maximal time during which device 140 completes the passage through the pre-designated anatomical structure or region.

currentTime may be the current time (e.g., in hours) of the captured image frame.

$EngSt_{LFR}$ may be the average energy needed to capture each frame, e.g., including illuminating, imaging, processing, and transmitting for each frame, in the minimum capture rate mode.

$T_{LFR}$ may be the time (e.g., in hours) interval for capturing one frame in the minimum capture rate mode.

Other parameters and other equations may be used. According to equation (1), the available energy remaining in the device power supply 145 (e.g., the difference between the initial energy supply or "BatteryFullCap" and the total energy usage "UsedEnergyTillNow" and the energy depletion due to storage "StorageEnergyReduction") may be greater than or equal to the energy needed to capture image frames at a minimum frame rate until the complete passage of 140 device (e.g., $$(ProcedureMaxTime - currentTime) * \frac{EngSt_{LFR}}{T_{LFR}}).$$

When the available energy is greater than the energy needed by at least the amount of energy used to capture an image at a medium or high frame rate, the medium or high frame rate may be used, respectively. When the available energy is equal to the energy needed, device 140 may switch to the minimum or least frame rate.

The following description provides demonstrative examples for operating device 140 according to embodiments of the invention, for example, using equation (1). It may be appreciated that these computations are generally executed by a processor in a computing device and that the representations of these values, order of operations, and other features may be different in different embodiments, e.g., in programming code with storage memory pointers. However, generally the same calculations may be used. It may be noted that the values given here are merely used for demonstration and different values may be used.

EXAMPLE 1

In a first example, power source 145 may have substantially no energy loss due to storage, e.g., when device 140 is immediately used, (StorageEnergyReduction==0). The energies used to capture each frame in each of modes 0-4 are described in Table 1. A clock in or operated by for example processor 147 (e.g., a 8.1 MHz clock) may measure the time in which device 140 operates each mode, e.g., as follows:

7 min in Mode 0 (1680 frames),
30 minutes in Mode 1 (1440 frames),
1 hour in Mode 2 (14400 frames),
57.4917 minutes in Mode 3 (124182 frames), and
a total estimated procedure time of 9 hours.

A processor may substitute the values above into equation (1), for example, as follows:

$$52 - 0 - \left(\frac{1.0993}{3600} * 1680 + \frac{0.6026}{3600} * 1440 + \frac{1.0993}{3600} * 14400 + \frac{0.5391}{3600} * 124182\right) - (9 - 2.5749) * \frac{\frac{1.0993}{3600}}{\frac{1}{4*3600}} =$$

$$52 - \left(\frac{1.0993}{3600} * 1680 + \frac{0.6026}{3600} * 1440 + \frac{1.0993}{3600} * 14400 + \frac{0.5391}{3600} * 124182\right) - (9 - 2.5749) * 4 * 1.0993 = 0.000049$$

The resulting equation (1) has a value very close to zero, though greater than zero (e.g., 0.000049). According to the energy usage values for each of the operational modes 0-4 in Table 1, if device 140 captured one more frame in Mode 3, equation (1) would have a value less than zero, indicating that the energy reserve is being depleted and device 140 may not have enough energy to capture frames for the total estimated procedure time of 9 hours. To ensure continued imaging for the entire length of the procedure, device 140 switches from the relatively high frame rate (e.g., 36 frames per second) in Mode 3 to at the minimal allowable frame rate (e.g., 4 frames per second) in Mode 2.

It may be appreciated that in some embodiments, the processor may switch to a minimum frame rate not before, but only after, an initial depletion of the energy reserve, e.g., when equation (1) first has a negative value. In this case, device 140 may capture frames for a time of only slightly less than (e.g., one or a few frames less than) the entire estimated procedure time (e.g., 9 hours). In this case, device 140 may capture frames for substantially, though not exactly, the total estimated procedure time.

A processor may proceed, for example, according to the following steps 1-3 written in pseudo-code:

Step 1. Determine the "EnergyBalance" of device 140 by subtracting the energy depleted due to storage time from the full initial energy of the power source 145, for example, as follows:

EnergyBalance=BatteryFullCap−
   StorageEnergyReduction=BatteryFullCap−
   (BSDF+COMC)*TotalMonths The processor may execute the following operations to retrieve data:
a. getBatteryCapacity( ): retrieve the full initial energy of power source 145 (e.g., stored as one (1) byte of telemetry data). This value may be set to 'BatteryFullCapacity' in equation (1).
b. getCurrentDate( ): used in storage time calculation for "TotalMonths" value above.
c. getProductionDate( ): used in storage time calculation for "TotalMonths" value above.
d. getBatteryBUC( ): retrieve the battery self discharge factor (BSDF) and the energy depletion over time (e.g., the capsule off current monthly consumption (COMC)) for power source 145. These parameters may be stored as a battery utilization coefficient or "BUC" in telemetry data, which may be one (1) byte).

The processor may determine the term $$EngPerTInLFR = \frac{EngSt_{LFR}}{T_{LFR}}.$$

This calculation may be executed in step 1 to enable fast multiplication in later steps, although alternatively, this calculation may be executed later.

The processor may execute the following operation to set the mode of device 140 to a relatively high frame rate mode, e.g., Mode 3 in Table 1, for example, as follows:

m_statusLowPower=HIGH POWER.

Setting the device to a higher than minimum frame rate may mean that the device 140 is allowed to, but will not necessarily, use the high frame rate. The energy evaluation, e.g., using equation (1) may define the energy modes available to device 140 so that its energy reserve is maintained. From among the available energy modes, the processor may determine the actual energy mode for device 140 to use, e.g., based on capture rate optimization parameter(s) (e.g., speed, color, texture, presence of villi, etc.). Once there is sufficient energy available for device 140 to be in a higher than minimum frame rate without depleting energy reserves, device 140 may toggle between the higher than minimum frame rate (e.g., Mode 3 at 36 frames per second) and the minimum frame rate (e.g., Mode 2 at 4 frames per second), e.g., for example, depending on sensed values of the frame capture rate parameter(s).

Step 2. For each frame captured and transmitted, the processor may subtract the energy of the transmitted frame in the current mode of the device from the "EnergyBalance". This energy may be pre-set and stored in a look-up table accessible by the processor (e.g., example values are listed in Table 1). In this way, the "EnergyBalance" value may be updated after each frame is captured and transmitted to represent the current amount of energy in power source 145.

Step 3. The processor may execute the following operation, for example, as follows:
a. LeftTime=ProcedureMaxTime-currentTime; ProcedureMaxTime may be retrieved from predefined settings associated with a type or model of device 140 or selected type of procedure. The predefined settings may be stored in a file in workstation 117 or receiving unit 112 and may be downloaded to the receiving unit 112.

b. NeededEnrToCompleteProc=LeftTime*EnrPerTInLFR; where EngPerTInLFR may be calculated to be $$EngPerTInLFR = \frac{EngSt_{LFR}}{T_{LFR}},$$

for example, as described in step 1.
c. If the total energy remaining is less than the energy reserve needed to complete the capture at a minimum frame rate, i.e., (EnergyBalance< NeededEnrToCompleteProc), then the device 140 mode may be permanently set to the mode with the minimum frame rate, for example: m_statusLowPower=LOW_POWER. Accordingly, only the minimum frame rate mode (LFR) may be enabled until substantially the end of the operation and/or the full depletion of power source 145.

Other operations of orders of operations may be used.

In some embodiments, if there is sufficient energy for device 140 to use a higher than minimum frame rate (e.g., Mode 3 at 36 frames per second or Mode 4 at 20 frames per second), the maximal number, X, of frames that may be captured at the higher than minimum frame rate may be determined, for example, by analyzing equations (2) and (3) defined as follows (other series of operations may be used):

$$BaseEnergy - X*EngStHFR - NumberOfFramesInLFR*EngStLFR \geq 0 \qquad Eq(2)$$

$$NumberOfFramesInLFR = (ProcedureMaxTime - TAFRStart - X*T_{HFR})/T_{LFR} \qquad Eq(3)$$

Parameters in equations (2) and (3) may be defined, for example, as follows:
BaseEnergy may be: [BatteryFullCap−StorageEnergyReduction−UsedEnergyTillNow]. This is the energy that the device 140 may use without depleting the energy reserve.
X may be the maximal number of frames that may be captured in a higher than minimum frame rate mode, e.g., Mode 3 or 4.
EngStHFR may be the energy used to capture each frame in the higher than minimum frame rate of Mode 3 or 4.
EngStLFR may be the energy used to capture each frame in the minimum frame rate of Mode 2.
ProcedureMaxTime may be the total estimated procedure time.
TAFRStart may be the time that the AFR is started.
$T_{HFR}$ may be the cycle time to capture one frame in the higher than minimum frame rate mode.
$T_{LFR}$ may be the cycle time to capture one frame in the higher than minimum frame rate mode.

Combining equations (2) and (3) may provide the following equation (4), which defines the maximum number or the upper limit of the number of frames, X, that may be captured in a higher than minimum frame rate mode, e.g., Mode 3 or 4, as follows:

$$X \leq \frac{BaseEnergy - \frac{ProcedureMaxTime - TAFRStart}{T_{LFR}} * EngSt_{LFR}}{EngSt_{HFR} - \frac{T_{HFR}}{T_{LFR}} * EngSt_{LFR}} \qquad Eq(4)$$

The following examples may be applied to evaluate equation (4).

EXAMPLE 2

In a second example, power source 145 may suffer an energy loss due to storage, e.g., when device 140 has been stored for 12 months. The average energies used to capture each frame in each of modes 0-4 are listed in Table 1. A clock in processor 147 (e.g., a 8.1 MHz clock) may measure the time in which device 140 operates each mode, e.g., as follows:
  7 min in Mode 0 (1680 frames),
  30 minutes in Mode 1 (1440 frames), and
  a total estimated procedure time of 9 hours.
A processor may calculate the BaseEnergy (mAh) of device 140, e.g., as follows:

$$BaseEnergy = \\ BatteryFullCap - StorageEnergyReduction - \sum_i EngSt_i * Counter_i = \\ 52 - (0.52 + 0.219) * 12 - \frac{1.0993}{3600} * 1680 - \frac{0.6026}{3600} * 1440 = \\ 42.378 \text{ mAh}$$

The processor may determine the maximal number, X, of frames that may be captured at the higher than minimum frame rate, e.g., of Mode 3, without depleting the energy reserve, when device 140 was stored for 12 months, e.g., by substituting values into equation (4) as follows.

$$X \leq \frac{BaseEnergy - \frac{ProcedureMaxTime - TAFRStart}{T_{LFR}} * EngSt_{LFR}}{EngSt_{HFR} - \frac{T_{HFR}}{T_{LFR}} * EngSt_{LFR}}$$

$$X = \frac{42.378 - \frac{9 - 0.6167}{0.25/3600} * 1.0993/3600}{0.5391/3600 - \frac{4}{36} * 1.0993/3600} = \frac{\left(42.378 - \frac{9 - 0.6167}{0.25} * 1.0993\right) * 3600}{0.5391 - \frac{4}{36} * 1.0993} = 47616$$

The value, X, of 47616 frames may be captured at the higher than minimum frame rate, e.g., of Mode 3, while maintaining the energy reserve necessary for the continued capture in the minimum frame rate, e.g., of Mode 2, for the remainder of the 9 hour procedure. In mode 3, since 36 frames are captures per second, device 140 may capture frames at this rate for a maximum of 22.5 minutes and then switch to the minimum frame rate, e.g., of Mode 2, for the remainder of the 9 hour procedure.

EXAMPLE 3

In a third example, power source 145 may have substantially no energy loss due to storage, e.g., when device 140 is used soon after manufacture, (StorageEnergyReduction=0). The energies used to capture each frame in each of modes 0-4 are listed in Table 1. A clock in processor 147 (e.g., a 8.1 MHz clock) may measure the time in which device 140 operates each mode, e.g., as follows:
  7 min in Mode 0 (1680 frames),
  30 minutes in Mode 1 (1440 frames), and
  a total estimated procedure time of 9 hours.
If there is no energy loss due to storage, the BaseEnergy (mAh) of device 140 may be calculated, e.g., as follows:

$$BaseEnergy = \\ BatteryFullCap - StorageEnergyReduction - \sum_i EngSt_i * Counter_i = \\ 52 - 0 - \frac{1.0993}{3600} * 1680 - \frac{0.6026}{3600} * 1440 = 51.246 \text{ mAh}$$

With no energy depletion due to storage, e.g., values may be substituted into equation (4) as follows:

$$X \leq \frac{BaseEnergy - \frac{ProcedureMaxTime - TAFRStart}{T_{LFR}} * EngSt_{LFR}}{EngSt_{HFR} - \frac{T_{HFR}}{T_{LFR}} * EngSt_{LFR}}$$

$$X = \frac{51.246 - \frac{9 - 0.6167}{0.25/3600} * 1.0993/3600}{0.5391/3600 - \frac{4}{36} * 1.0993/3600} = \frac{\left(51.246 - \frac{9 - 0.6167}{0.25} * 1.0993\right) * 3600}{0.5391 - \frac{4}{36} * 1.0993} = 124182$$

The value, X, of 124182 frames may be captured at the higher than minimum frame rate, e.g., of Mode 3, while maintaining the energy reserve necessary for the continued capture in the minimum frame rate, e.g., of Mode 2, for the remainder of the 9 hour procedure. In mode 3, since 36 frames are captures per second, device 140 may capture frames at this rate for a maximum of 57 minutes and then switch to the minimum frame rate, e.g., of Mode 2, for the remainder of the 9 hour procedure.

Additional mechanisms to reduce power in device 140 may include, for example, the following:
  Received signal strength indicator (RSSI) optimization: based on the amount of energy left and an estimation of the amount of energy required for completing the procedure (i.e., completing optimal coverage of the selected organ of interest), receiving unit 112 may determine whether the received signal strength is above a certain threshold, and if so, the transmission strength of device 140 may be reduced. Embodiments of the invention for reducing transmission power based on RSSI optimization may be used, for example, as described in U.S. Pat. No. 6,934,573 to GLUKHOVSKY et al., entitled "SYSTEM AND METHOD FOR CHANGING TRANSMISSION FROM AN IN VIVO SENSING DEVICE," which is hereby incorporated by reference in its entirety.
  Light optimization (ALC): to reduce the amount of energy or current provided to the illumination sources 142 (based on image intensity/brightness). Embodiments of the invention for reducing illumination levels according to image saturation may be used, for example, as described in U.S. Patent Application Publication No. 20030/117491 to Avni et al., entitled "APPARATUS AND METHOD FOR CONTROLLING ILLUMINATION IN AN IN VIVO IMAGING DEVICE," which is hereby incorporated by reference in its entirety.

Adaptive frame rate for maintaining a minimum capture rate through the entire area of interest as described according to embodiments of the invention.

Adaptive frame rate for reducing the frame rate when device 140 is stopped or not in motion. Embodiments of the invention for reducing the frame rate may be used, for example, as described in U.S. Pat. No. 7,022,067 to GLUKHOVSKY et al., entitled "SYSTEM FOR CONTROLLING IN VIVO CAMERA FRAME CAPTURE AND FRAME DISPLAY RATES," which is hereby incorporated by reference in its entirety.

Using smart batteries which may indicate power source 145 status, alerts, or an estimated power life according to a rate of current usage. Embodiments of the invention describing a smart battery may be used, for example, as described in U.S. Patent Application Publication No. 2007/0232887 to Khait et al., entitled "SYSTEM AND METHOD FOR CHECKING THE STATUS OF AN IN VIVO IMAGING DEVICE," which is hereby incorporated by reference in its entirety.

Monitoring the voltage of power source 145 to estimate its power life under a specific load of operation(s).

In some embodiments, other frame rates may be used, and the modes may be activated for different periods of time. For example, the device 140 may be operated in mode 0 (e.g. 4 frames per second) for a period of 3 minutes, in mode 1 for a period of 30 minutes (14 frames per minute), and for the rest of the procedure, the modes may be switched between mode 2 (e.g. 4 frames per second) and mode 3 (e.g. 35 frames per second), depending on, for example, the motility of the device, its speed or acceleration, or on a change in scenery between sequential frames. A total estimated time of the imaging procedure may be, for example, 5 hours. Other parameters may of course be used.

Figure 3:
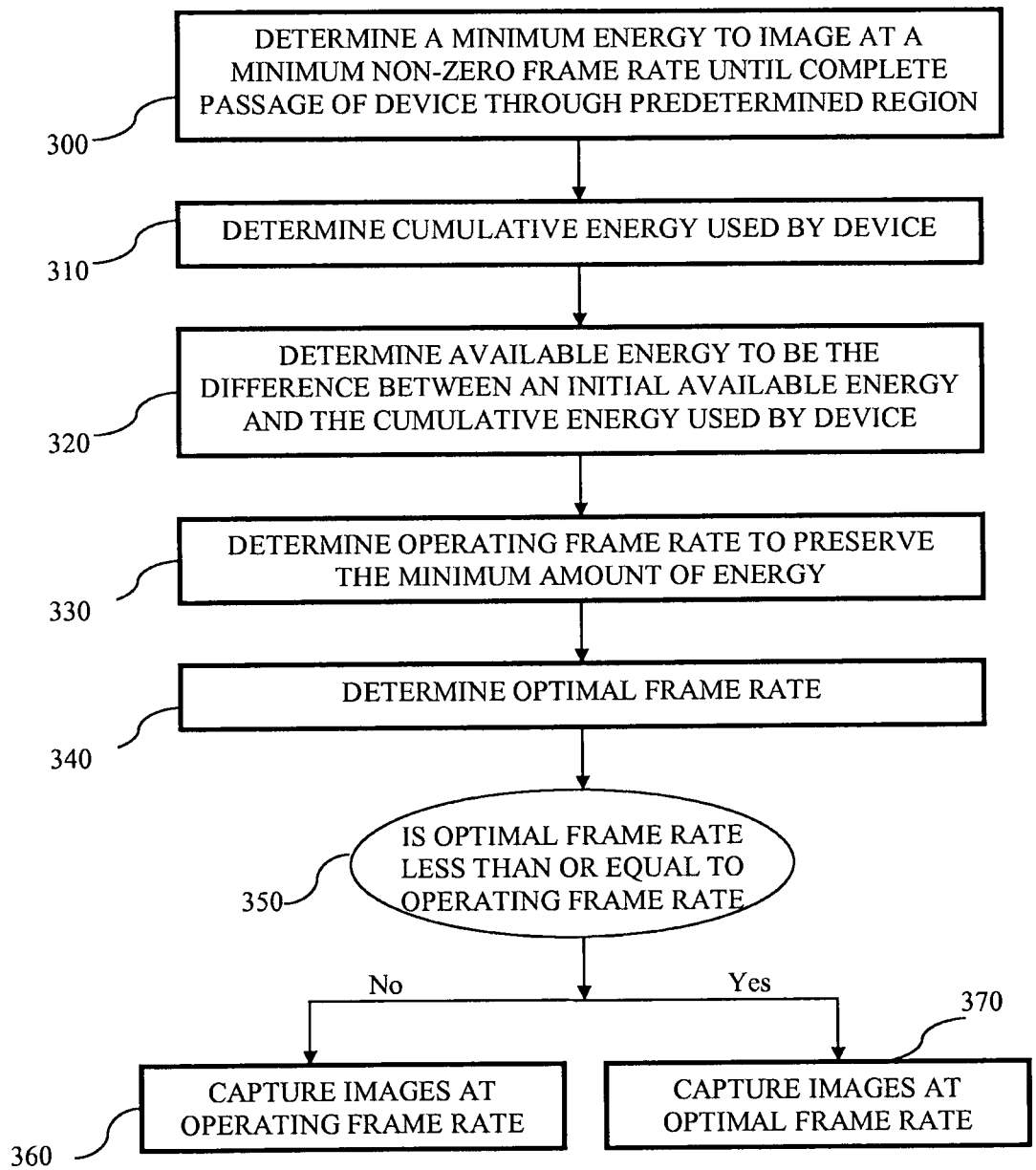
FIG. 3 is a simplified flowchart illustration of a method of performing frame rate control by an in vivo imaging device according to an embodiment of the invention.

Reference is made to FIG. 3, which is a flowchart of a method of performing frame rate control by an in vivo imaging device in accordance with some embodiments of the present invention.

In operation 300, a processor or process (e.g., processor 122, 114, and/or 147 of FIG. 1) may determine a minimal amount of energy needed to capture image frames at a minimum non-zero frame rate until the complete passage of the device through at least a predetermined region of the GI tract. A minimum amount of energy may be an amount of energy reserved in the power supply that may remain unused to ensure that it is available in the future to capture one or more subsequent images at a minimum or least frame rate (LFR) until the estimated end of the body region or passage. Over time, as an in vivo device (e.g., device 140 of FIG. 1) progresses along the GI tract, the device may need less and less energy in the reserve to finish capturing images at the LFR. Therefore, the minimum energy may decreases to zero at the estimated time at which the procedure ends (when no reserve energy is needed).

In operation 310, the processor or process may estimate or determine an approximation of the cumulative amount of energy used during the operation of the device. The cumulative amount of energy may be calculated based on, for example, averages of energies used by an illumination source, imager, processor, and transmitter. In some embodiments, the processor may estimate an amount of energy to be used during the remaining time duration of operation of the device, until completion of the imaging procedure of the imaged organ or maximum estimated time of completion. This amount may be measured, e.g., via signals from a battery, or calculated, e.g., based on a known amount of energy used per frame times the number of frames captured.

In operation 320, the processor or process may determine the available energy remaining in the device power supply. In one embodiment, the available energy remaining in the device power supply may be estimated to be the difference between an initial available energy in the device power supply and the approximated cumulative energy used, e.g., determined in operation 310. In another embodiment, the available energy remaining in the device power supply may be determined based on a signal transmitted from the battery, or by comparing a current voltage level of the battery with a previous voltage level or an initial voltage level.

The available amount of energy in operation 320 may be the inversely proportional to the cumulative amount of energy used in operation 310. For example, as the cumulative amount of energy used increases, the available amount of energy typically decreases. In one embodiment, the available energy may be equal to the total initial energy (e.g., known based on the battery source specification) less the cumulative amount of energy used (310)). In some embodiments, one of operations 310 and 320 need not be used and determining one of the available energy or cumulative energy used may be equivalent to determining the other. For example, if the energy remaining is determined by using a battery voltage, the cumulative energy used need not be used.

In operation 330, the processor or process may determine an operating frame rate that uses an amount of energy from the device power supply so that the available energy remaining in the device power supply is sufficient for completing the imaging procedure, e.g. greater than or equal to the minimal amount of energy.

The processor or process may, for example, determine a minimal amount of energy needed to operate the in vivo imaging device at a minimum non-zero frame capture rate to complete a passage of the device through at least a predetermined region of the GI tract.

Over time as images are captured along the body passageway, the cumulative energy used (in operation 310) increases and the available energy (in operation 320) decreases. An operating frame rate for capturing subsequent images (or similarly the time interval till the next frame is captured) may be selected that is estimated to use an amount of energy or depletes the available energy to maintain the minimal amount of energy reserve (in operation 300). For example, the available amount of energy (in operation 320) less the calculated energy for capturing subsequent images at the operating frame rate may be greater than or equal to the minimal amount of energy (in operation 300). Equivalently, the total initial energy less the calculated energy for capturing subsequent images at the operating frame rate and less the cumulative amount of energy used (in operation 310) may be greater than or equal to the minimal amount of energy (in operation 300). The operating frame rate may be the maximum allowable (upper limit) frame capture rate to maintain the energy reserve (e.g., the lower limit or minimum allowable frame capture rate may be the LFR).

In operation 340, the processor may determine an optimal frame rate. The optimal frame rate may be determined based on, for example, degree of similarity between sequential frames, detection of pathology in frames, device speed or a degree of acceleration and/or rotation motion, color, hue, saturation, texture or patterns in images or between sequential images, impedance variation, pH, etc. The processor or process may, for example, determine an operating frame rate for capturing one or more subsequent images that uses a calculated total amount of energy from the device power supply, wherein the available energy remaining in the device power supply less (having subtracted from it) the calculated total amount of energy is greater than or equal to the minimal amount of energy.

In operation 350, the processor or process may determine if the optimal frame rate is less than or equal to the operational frame rate. If not, a process may proceed to operation 360. If yes, the process may proceed to operation 370. The processor or process may cause an in vivo device or imager to operate at a certain frame rate.

In operation 360, when the optimal frame rate is greater than the operational frame rate, an imager (e.g., imager 146 of FIG. 1) may capture subsequent one or more images at the operational frame rate determined in operation 330. The operating frame rate of operation 330 may define a maximum allowable frame rate. In this case, since the optimal frame rate is greater than this upper bound operating frame rate of 330, capturing subsequent images at this optimal frame rate would deplete the energy reserve and should be avoided.

In operation 370, when the optimal frame rate is less than or equal to the operational frame rate, the imager may capture subsequent one or more images at the optimal frame rate determined in operation 340. In this case, since the optimal frame rate is less than or equal to the upper bound operating frame rate of 330, capturing subsequent images at this optimal frame rate would not deplete the energy reserve.

Other operations or series of operations may be used.

It may be appreciated that although specific reference is made to regions of the body, such as the colon, small bowel, stomach, etc., these regions are merely demonstrative and the descriptions associated with any or each of these regions may be interchanged or instead associated with other segments of a body passage of any length or other pre-designated time intervals.

Although the particular embodiments shown and described above will prove to be useful for the many distribution systems to which the present invention pertains, further modifications of the present invention will occur to persons skilled in the art. All such modifications are within the scope and spirit of the present invention as defined by the appended claims.

What is claimed is:

1. A method for controlling energy consumption of an in vivo imaging device, the method comprising:
   repeatedly calculating a minimal amount of energy needed to operate the in vivo imaging device at a minimum non-zero frame capture rate to complete a passage of the device through at least a predetermined region of the GI tract;
   calculating the amount of available energy remaining in the device power supply, based on an amount of energy associated with capturing a frame and the number of frames captured;
   when the amount of available energy remaining in the device power supply is greater than the minimal amount of energy, enabling operation of the device at a frame capture rate above the minimum non-zero frame capture rate;
   and
   when the available energy remaining in the device power supply is not greater than the minimal amount of energy, operating the device at the minimum non-zero frame capture rate.

2. The method of claim 1, wherein the capture rate above the minimum non-zero frame capture rate is determined based on at least one of the elements from the group consisting of: degree of similarity between sequential captured frames, detection of pathologies in frames, device speed or a degree of acceleration and/or rotation motion, color, hue, saturation, texture or patterns in images or between sequential images, impedance variation, and pH.

3. The method of claim 1, wherein the capture rate above the minimum non-zero frame capture rate is at least partially determined based on the anatomical region of the body where the device is located.

4. The method of claim 1, wherein the difference between an initial useable energy held in a power source of the device and an accumulated amount of energy used during device operation never exceeds the amount of energy needed to continue capturing image frames until the complete passage of the device in a region of interest.

5. The method of claim 1, comprising, determining an approximation of the cumulative amount of energy used during the operation of the device based on averages of energies used by an illumination source, imager, processor, and transmitter and wherein the available energy remaining in the device power supply is calculated to be the difference between an initial available energy and the approximated cumulative energy used.

6. The method of claim 1, wherein the capture rate above the minimum non-zero frame capture rate is relatively higher when the device is located in a predefined region of interest than in any other region of the GI tract.

7. The method of claim 1, wherein the capture rate above the minimum non-zero frame capture rate is relatively lower when the device is located in the small bowel compared to when the device is located in the colon.

8. The method of claim 1, wherein the capture rate above the minimum non-zero frame capture rate is relatively lower when the device is located in the stomach as compared to when the device is located in the colon or the small bowel.

9. The method of claim 1, comprising, when the device passes from the stomach to the small bowel, increasing the capture rate above the minimum non-zero frame capture rate from a first frame rate to a second frame rate.

10. The method of claim 9, comprising, when the device passes from the small bowel to the colon, increasing the capture rate above the minimum non-zero frame capture rate from the second frame rate to a third frame rate.

11. The method of claim 1, comprising determining a maximum duration of the complete passage of the device through the predetermined region of the GI tract to be imaged.

* * * * *